(12) United States Patent
Dupret et al.

(10) Patent No.: US 7,303,897 B2
(45) Date of Patent: Dec. 4, 2007

(54) METHOD OF PREPARING POLYNUCLEOTIDE FRAGMENTS FOR USE IN SHUFFLING, AND SHUFFLING OF SAME

(75) Inventors: Daniel Dupret, Calvisson (FR); Fabrice Lefevre, Bajonnette (FR); Laurent Fourage, Calvisson (FR)

(73) Assignee: Proteus S.A., Nimes (FR)

( * ) Notice: Subject to any disclaimer, the term of this patent is extended or adjusted under 35 U.S.C. 154(b) by 206 days.

(21) Appl. No.: 10/713,006

(22) Filed: Nov. 17, 2003

(65) Prior Publication Data

US 2004/0214197 A1 Oct. 28, 2004

Related U.S. Application Data

(63) Continuation of application No. PCT/IB02/02769, filed on May 16, 2002.

(60) Provisional application No. 60/291,184, filed on May 17, 2001.

(51) Int. Cl.
*C12P 19/34* (2006.01)
*C12N 15/01* (2006.01)

(52) U.S. Cl. ............ 435/91.1; 435/441; 435/442; 435/443; 435/444; 435/445

(58) Field of Classification Search ............ None
See application file for complete search history.

(56) References Cited

U.S. PATENT DOCUMENTS 5,556,750 A 9/1996 Modrich et al.
5,605,793 A 2/1997 Stemmer
5,830,721 A 11/1998 Stemmer et al.
5,965,408 A 10/1999 Short
6,537,746 B2 * 3/2003 Arnold et al. ............ 435/6

FOREIGN PATENT DOCUMENTS

WO WO97/21537 A1 6/1997
WO WO99/29902 A1 6/1999

OTHER PUBLICATIONS

Stemmer et al. Proc. Natl. Acad. Sci. 1994; 91: 10747-51.*
Tsai-Wu et al. (Analytical Biochemistry, 1999, 275: 127-129).*
Dianov et al, "Reconstitution of the DNA base excision-repair pathway", *Current Biology* (1994), vol. 4, No. 12, pp. 1069-1078.
Stemmer, W., "DNA shuffling by random fragmentation for molecular evolution", *National Academy of Sciences* (Oct. 1, 1994), vol. 91, pp. 10747-10751, Washington. XP002087463.

* cited by examiner

*Primary Examiner*—Daniel M Sullivan
(74) *Attorney, Agent, or Firm*—Hunton & Williams LLP (57) ABSTRACT

The invention relates to a fragmentation process that depends on mismatches between two strands of parental polynucleotides. One embodiment, comprises a method for preparing polynucleotide fragments of DNA comprising formation of heteroduplex molecules by hybridizing polynucleotides. The invention also provides a method and process of forming fragments which can be used with any shuffling process or combination of shuffling processes.

12 Claims, 6 Drawing Sheets

METHOD OF PREPARING POLYNUCLEOTIDE FRAGMENTS FOR USE IN SHUFFLING, AND SHUFFLING OF SAME

CROSS-REFERENCE TO RELATED APPLICATIONS

This application is a continuation of International Application No. PCT/IB02/02769, filed May 16, 2002, which was published in English and claimed priority to provisional application 60/291,184 filed on May 17, 2001 and is hereby incorporated by reference in its entirety.

BACKGROUND OF THE INVENTION

Methods of directed evolution employing DNA or polynucleotide repair to mediate the creation of genetic diversity are known in the art. For example, such a method is described in WO 99/29902, which is expressly incorporated herein in its entirety. These types of methods consist of exposing a heteroduplex polynucleotide to a cellular DNA repair system to either fully convert one strand of the heteroduplex to the perfect complement of the opposing strand or to partially convert one or both strands to the more perfect complement of the other, thereby forming in the latter case a recombinant heteroduplex.

In many ways, however, the particular use of DNA repair described above does not lend itself to shuffling-based methods of directed evolution, especially those methods that are template-mediated. First, in template-mediated methods of shuffling the recombinant strand that forms on the template strand should not, of course, be repaired to the point where it becomes identical to the template strand. Second, depending on the reaction conditions and starting materials the template strand might be inadvertently repaired to match the recombinant strand, which is especially disadvantageous if the template is to be recycled or used again. Thus, using DNA repair as described above would require close monitoring of the starting materials, conditions of the repair reactions and the amounts of repair enzymes. Third, using DNA repair as described above places the experimenters means of control at a point toward the end of the process, that is, not until after the shuffling and the annealing of the recombinant strand to the template. As explained below, there are advantages to moving the means of control to a point before the shuffling or creation of the fragments.

Moreover, the use of DNA repair described in WO 99/29902 does not suggest an alternative use for DNA repair, perhaps because the alternative use only makes sense in the context of shuffling-based methods of directed evolution. The alternative is use of DNA repair proteins not to repair polynucleotides per se but to fragment polynucleotides.

Cellular DNA is constantly exposed to a wide spectrum of exogenous factors (e.g., ultraviolet light, ionizing radiation, or environmental chemicals) or endogenous factors (e.g., oxidative damage, or structural instability at physiological pH) that generate DNA lesions. To counteract these factors, a variety of DNA repair pathways have evolved to protect the cell against the genotoxic and lethal effects of DNA damage. DNA excision repair pathways include, for example, base excision repair (BER), nucleotide excision repair (NER), and mismatch repair (MMR).

Figure 1:
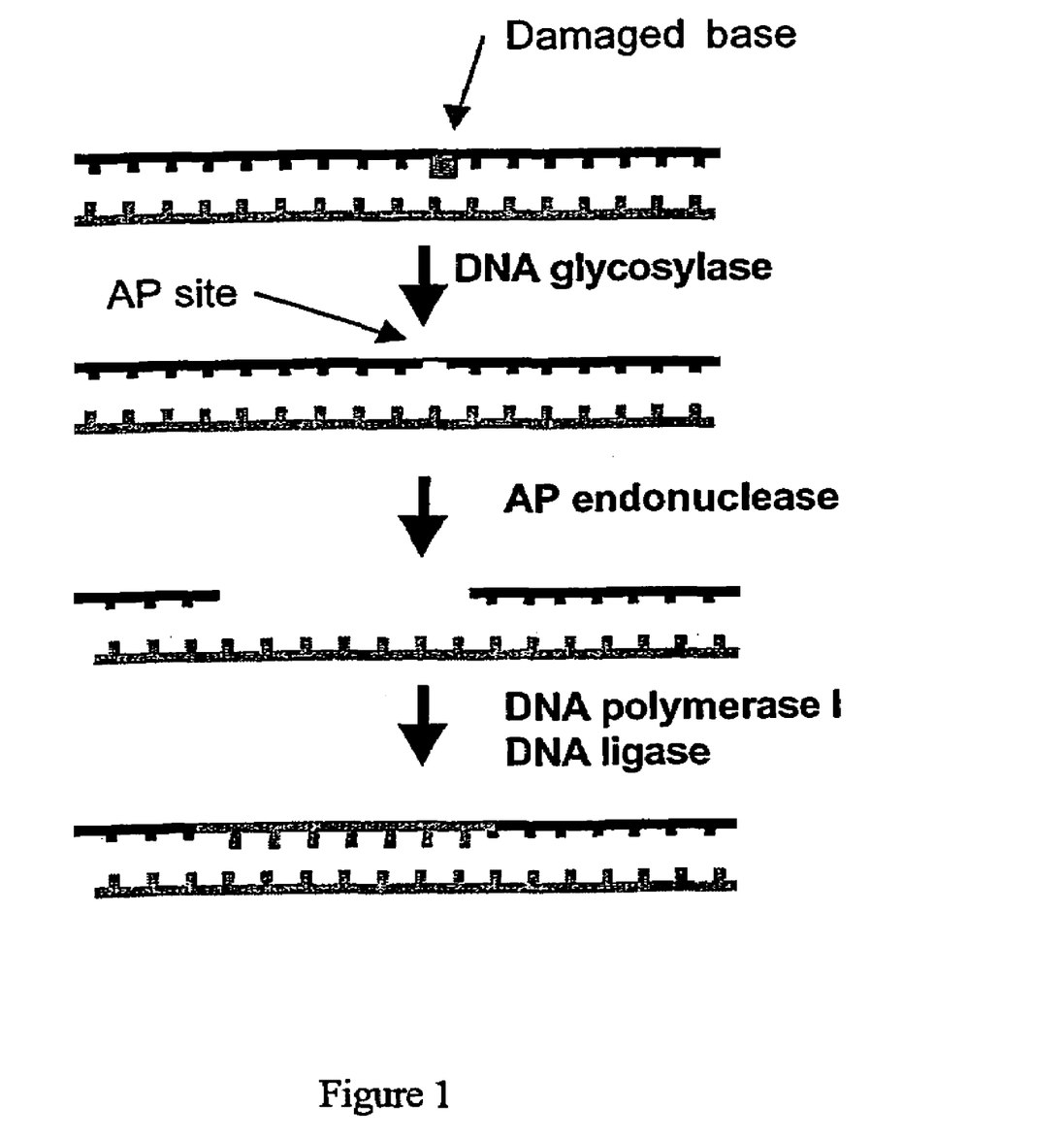
FIG. 1 depicts DNA repair by base excision.

In E. coli, for example, several proteins are involved in these three repair pathways. In the BER pathway, the involved proteins are DNA glycosylase, AP endonuclease, DNA polymerase I and ligase. The position of a damaged base is called the abasic site or AP site. The DNA glycosylase recognizes the AP site and removes the damaged base. Then, the AP endonuclease removes the AP site and neighboring nucleotides thereby creating an induced gap. Finally, the induced gap is filled by the DNA polymerase I and the DNA ligase. See FIG. 1.

Figure 2:
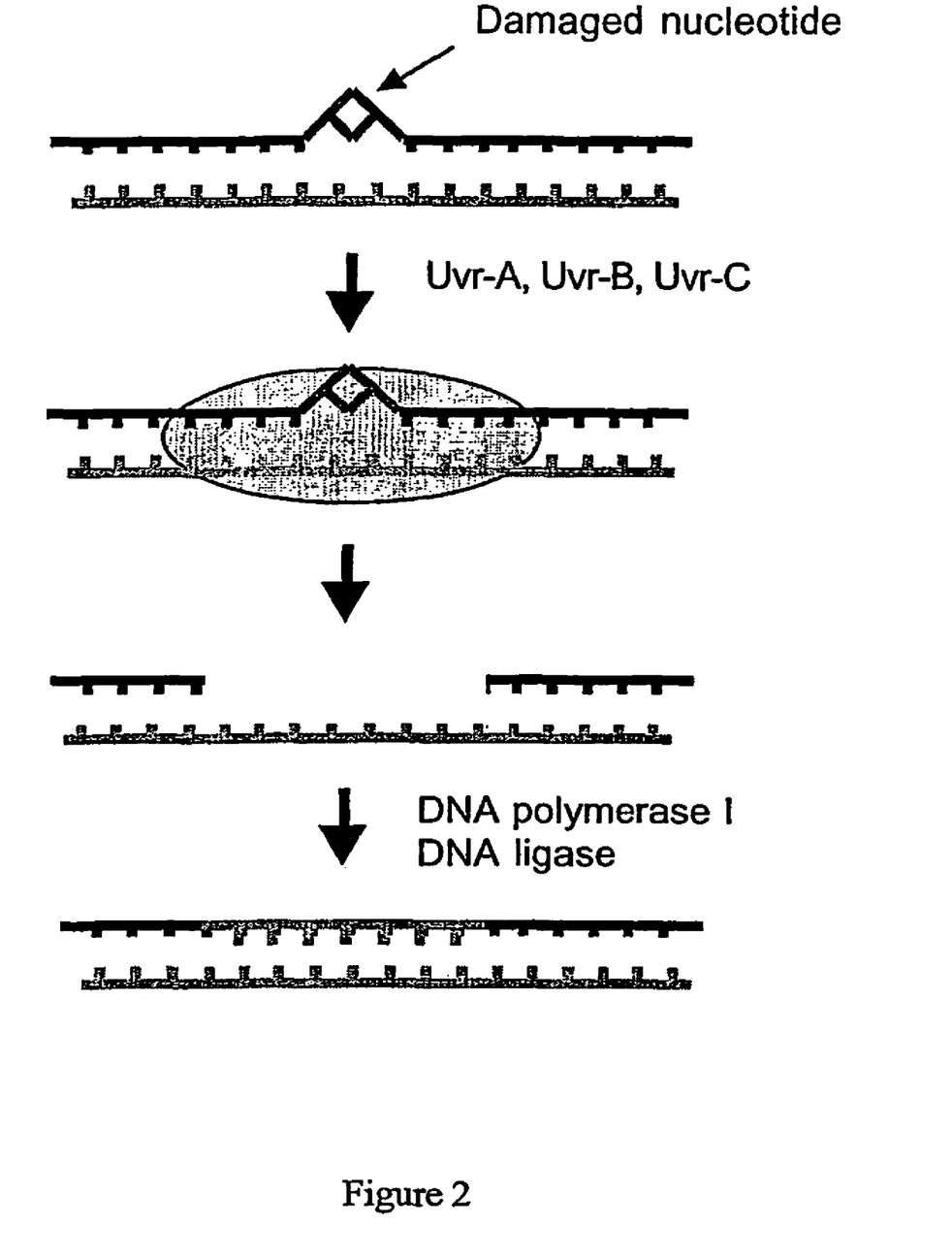
FIG. 2 depicts DNA repair by nucleotide excision.

In the NER pathway, the involved proteins in E. coli are Uvr-A, Uvr-B, Uvr-C, DNA polymerase I and DNA Ligase. Urn-A, Uvr-B, and Uvr-C are involved in removing of damaged nucleotides (e.g., dimers induced by ultraviolet light) to create an induced gap. The induced gap is filled by DNA polymerase I and DNA ligase. See FIG. 2. In yeast, proteins similar to those in E. coli are involved. For example, in yeast, RADxx (e.g., RAD3 and RAD10) proteins are similar to Uvr in E. coli.

In the MMR pathway, the involved proteins in E. coli are DAM methylase, MutS, MutL, MutH, exonuclease, DNA helicase II, SSB protein, DNA polymerase III and DNA ligase. To repair mismatched bases, the pathway involves a determination of which base is the correct one. In E. coli, this determination is achieved by a special methylase called Dam methylase, which can methylate all adenines that occur within (5')GATC sequences. Immediately after DNA replication, the template strand has been methylated, but the newly synthesized strand has not yet been methylated. Thus, the template strand and the new strand can be distinguished. Mismatch repair in eukaryotes may be similar to that in E. coli. Homologs of MutS and MutL have been identified in yeast, mammals, and other eukaryotes. MSH1 to MSH5 are homologous to MutS. MLH1, PMSI and PMS2 are homologous to MutL. In eukaryotes, the mechanism to distinguish the template strand from the new strand is still unclear.

Figure 3:
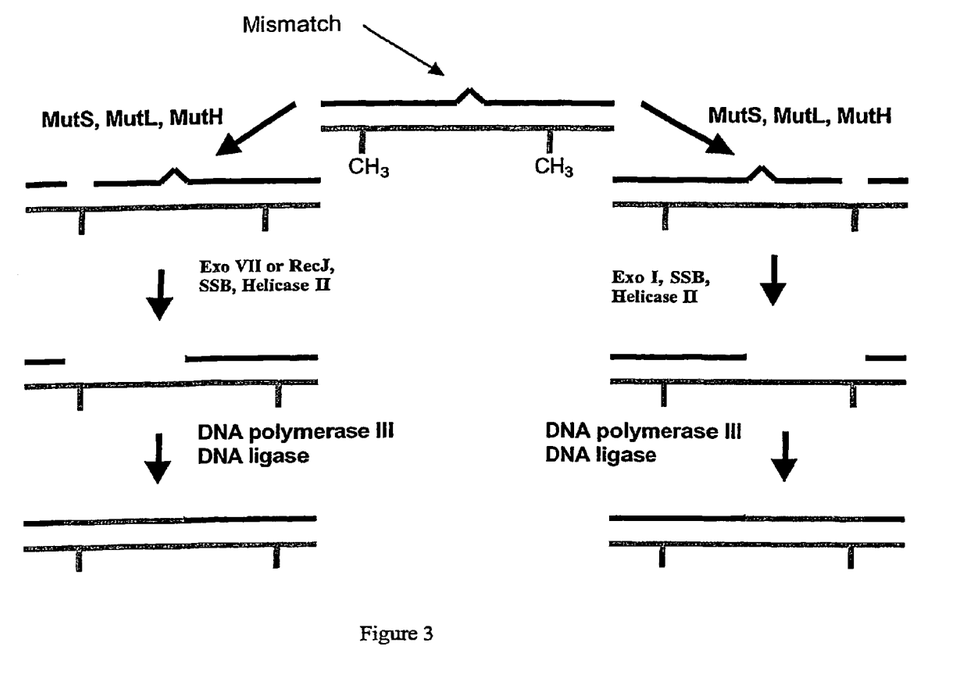
FIG. 3 depicts DNA repair by mismatch recognition.

The MMR pathway continues with the MutS binding to mismatched base pairs. See FIG. 3. MutL is then recruited to the complex and activates MutH which binds to GATC sequences. Activation of MutH cleaves the unmethylated strand at a GATC site. Subsequently, the segment from the cleavage site to the mismatch is removed by exonuclease. This step simultaneously involves helicase II and single strand DNA binding proteins. These single strand DNA binding proteins are called SSB proteins. If the cleavage occurs on the 3' side of the mismatch, the step is carried out by exonuclease I (which degrades a single strand only in the 3' to 5' direction). If the cleavage occurs on the 5' side of the mismatch, exonuclease VII or RecJ is used to degrade the single stranded DNA. The gap is filled by DNA polymerase III and DNA ligase. The distance between the GATC site and the mismatch can be as long as 1000 base pairs. Therefore, mismatch repair is very expensive and inefficient.

In vitro and in vivo recombination of nucleic acids have useful applications (e.g., creating novel sequences which encode proteins having desired or improved properties). A variety of methods have been described in the art to enable this recombination (e.g., rational design to directed evolution). These methods include those described in U.S. Pat. Nos. 5,605,793 and 5,965,408—which are herein incorporated by reference in their entirety. Generally, recombination methods depend on making fragments and recombining the fragments. With regard to recombining fragments, various methods have been described in the art. For example, U.S. Pat. Nos. 5,605,793 and 5,965,408 recite recombining fragments based upon polymerase chain reaction-like themocycling of fragments in the presence of DNA polymerase. International Patent No. WO 00/09679—which is herein incorporated by reference in its entirety—describes thermocycling ligation to recombine fragments of more specific and increased gene size. These methods rely on a multistep process involving a fragmentation step to generate fragments of parental genes that are further assembled to create recombined polynucleotides. Fragmentation is obtained by random treatments (e.g., DNAse I, sonication, mechanical disruption), or by controlled treatments (e.g., restriction endonucleases). These fragmentation processes do not take into account the level of homology of the parental genes.

Further general information regarding use of DNA repair systems in vitro appears in Dianov et al, *Curr. Biol.* 1994 (1069-1078), and in WO 97/21537, both of which are expressly incorporated herein in their entireties.

Definitions

In vitro, as used herein, refers to any location outside a living organism.

In vivo refers to any phenomena that occurs in a living organism, typically a cell.

DNA repair or polynucleotide repair refers to any processes that, in cells, protect against the genotoxic effects of DNA damage. Yet, in the present invention the repair preferably occurs in vitro.

ds means double stranded DNA.

ss means single stranded DNA.

Polynucleotide and polynucleotide sequence refer to any nucleic or ribonucleic acid sequence, including mRNA. A polynucleotide may be a gene or a portion of a gene. Gene refers to a polynucleotide or portion thereof associated with a known or unknown biological function or activity. Thus genes include coding sequences, regulatory sequences and recognition sequences. A gene can be obtained in different ways, including extraction from a nucleic acid source, chemical synthesis and synthesis by polymerization.

Homologous polynucleotides differ from each other at least at one corresponding residue position. Thus, as used herein, homologous encompasses what is sometimes referred to as partially heterologous. The homology, e.g., among the parental polynucleotides, may range from 20 to 99.99%, preferably 30 to 90, more preferably 40 to 80%. In some embodiments the term homologous may describe sequences that are, for example, only about 20-45% identical at corresponding residue positions. Homologous sequences may or may not share with each other a common ancestry or evolutionary origin.

Heteroduplex polynucleotides are double-stranded polynucleotides in which the two strands are not perfectly complementary to each other.

The phrase "at least two homologous heteroduplex polynucleotides" refers to a plurality of double-stranded polynucleotides, wherein a strand of each double-stranded polynucleotide is not only imperfectly complementary to its opposed strand, but also differs from the corresponding strand of one of the other double-stranded polynucleotides at least at one corresponding residue position. In other words, the heteroduplex polynucleotides are homologous to each other.

Parental polynucleotide and parent are interchangeable synonyms that refer to the polynucleotides that are fragmented to create donor fragments. In the present invention, the parental polynucleotides are generally homologous heteroduplex polynucleotides. Parental polynucleotides are often derived from genes. Recombined polynucleotide, mutant polynucleotide, chimeric polynucleotide and chimera generally refer to the polynucleotides that are generated by the method. However, these terms may refer to other chimeric polynucleotides, such as chimeric polynucleotides in the initial library. Reference sequence refers to a polynucleotide, often from a gene, having desired properties or properties close to those desired, and which is used as a target or benchmark for creating or evaluating other polynucleotides.

Polynucleotide library and DNA library refer to a group, pool or bank of polynucleotides containing at least two homologous polynucleotides, particularly homologous heteroduplex polynucleotides. A polynucleotide library may comprise either an initial library or a screening library. Initial library, initial polynucleotide library, initial DNA library, parental library and start library refer to a group, pool or bank of polynucleotides or fragments thereof containing at least two homologous parental polynucleotides or fragments thereof. The initial library may comprise genomic or complex DNA and include introns. It may also comprise sequences generated by prior rounds of shuffling. Similarly, a screening library or other limited library of recombinant polynucleotides or fragments may serve as and be referred to as an initial library. Screening library refers to the polynucleotide library that contains chimeras generated by the inventive process or another recombinant process.

Residue refers to an individual base, nucleotide or ribonucleotide, rather than to multiple bases, nucleotides or ribonucleotides. Residue may refer to a free residue that is not part of a polynucleotide or fragment, or to a single residue that forms a part of a polynucleotide or fragment.

Donor fragments and fragments generally refer to the fragmented portions of parental polynucleotides. Fragments may also refer to supplemental or substitute fragments that are added to the reaction mixture and/or that derive from a source other than fragmentation of the parental polynucleotides. Most or all of the fragments should be shorter than the parental polynucleotides. Most or all of the fragments are shorter than the assembly templates. As used herein, the donor fragments preferably do not initiate polymerase extension, i.e., they are not primers.

Nonrandom and controlled, as used herein, refer broadly to the control or predictability, e.g., over the rate or location of recombination, achieved via the template and/or ligation-orientation of the invention. Nonrandom and controlled may also refer more specifically to techniques of fragmenting polynucleotides that enable some control or predictability over the size or sequence of the resulting fragments. For example, using restriction enzymes to cut the polynucleotides provides some control over the characteristics of the fragments. Note that the invention may still be considered nonrandom when it employs random fragmentation (typically by DNase I digestion). In such cases, the assembly template, repair mechanisms and other features of the invention still provide a degree of control. In preferred embodiments, however, the fragmentation is nonrandom or controlled.

Assembly template and template refer to a polynucleotide used as a scaffold or matrix upon which fragments may anneal or hybridize to form a partiality or fully double-stranded polynucleotide. The assembly templates of the invention are to be distinguished from various sequences in the art that have been referred to as templates. For example, the templates of the present invention do not include overlapping donor fragments that facilitate the extension of complimentary donor fragments hybridized thereto. As such, the assembly template is distinct from the donor fragments at some point in the process. The assembly templates of the present invention also do not include those sequences used in processes that rely heavily on polymerase extension to generate all or most of the opposing strand. In other words, the shuffling embodiment of the invention relies on hybridization of donor fragments to from the brunt of the recombinant strand. Preferably, the template strand of the recombinant polynucleotide formed by the process, although it may itself be recombinant, does not undergo recombination during the process. In other words, preferably no donor fragments are incorporated into the template strand during a cycle of the process. The template may be synthetic, result from shuffling or other artificial processes, or it may exist in nature. Transient template refers to a template that is not itself incorporated-into the final recombinant polynucleotides. This transience is caused by separation or disintegration of the template strand of the nonfinal recombinant polynucleotide generated during the method. The template may derive from the reference sequence, the initial library, the screening library or elsewhere. Although the template may comprise or derive from a parental polynucleotide of the initial library, in a preferred embodiment the template is devised, and a polynucleotide does not qualify as a devised template if it enters the shuffling process accidentally, e.g., by somehow slipping into the hybridization step without being fragmented. In other words, a devised template is not entirely random or accidental. Rather, at least to some extent a devised template is directly or indirectly obtained for use as a template by a human being, or a computer operated thereby, via purposeful planning, conception, formulation, creation, derivation and/or selection of either a specific desired polynucleotide sequence(s) or a sequence(s) from a source(s) that is likely to contain a desired sequence(s).

Parental template refers to the strand of a parental polynucleotide or heteroduplex that is generally unaffected by the polynucleotide repair system, for example, because it is methylated. As such, parental template reflects the popular usage of the term template, in contrast to the more specialized meaning of assembly template as described above.

Solitary-stranded or non-identical is used to describe a population of single-stranded sequences that do not complement each other because they are all from the same strand, either sense or antisense, of one polynucleotide or multiple homologous polynucleotides. In other words, sequences from the opposing complementary strands are absent, so the population contains no sequences that are complementary to each other. For example, the population of non-identical fragments may consist of fragments of the top strands of the parental polynucleotides, whereas the population of non-identical templates may consist of bottom strands of one or more of the parental polynucleotides.

Ligation refers to creation of a phosphodiester bond between two residues.

Nick refers to the absence of a phosphodiester bond between two residues that are hybridized to the same strand of a polynucleotide. Nick includes the absence of phosphodiester bonds caused by DNases or other enzymes, as well as the absences of bonds between adjacently hybridized fragments that have simply not been ligated. As used herein, nick does not encompass residue gaps.

Gap and residue gap, as used herein, refer to the absence of one or more residues on a strand of a partially double-stranded polynucleotide. In some embodiments of the invention, short gaps (less than approximately 15-50 residues) are filled in by polymerases and/or flap trimming. Long gaps are conventionally filled in by polymerases.

Hybridization has its common meaning except that it may encompass any necessary cycles of denaturing and re-hybridization.

Adjacent fragments refer to hybridized fragments whose ends are flush against each other and separated only by nicks, not by gaps.

Ligation-only refers to embodiments of the invention that do not utilize or require any gap filling, polymerase extension or flap trimming. In ligation-only embodiments, all of the fragments hybridize adjacently. Note that embodiments that are not ligation-only embodiments still use ligation.

As used herein, ligation-oriented, oriented ligation and ligation-compatible generally represent or refer to a template-mediated process that enables ligation of fragments or residues in a relatively set or relatively predictable order. In ligation-only embodiments, the method employs no gap filling techniques and instead relies on ligation of adjacent fragments, often achieved after multiple hybridization events.

As used herein, exonuclease-mediated generally refers to a template-mediated process that employs flap trimming to enable ligation of fragments or residues in a relatively set or relatively predictable order.

BRIEF DESCRIPTION OF THE DRAWINGS

Reference is made to the appended drawings in which.

DETAILED DESCRIPTION OF THE INVENTION

This invention relates to a fragmentation process that depends on mismatches between two strands of parental polynucleotides. In one main embodiment, the invention comprises a method for preparing polynucleotide fragments of DNA comprising formation of heteroduplex molecules by hybridizing polynucleotides. These polynucleotides may be single-stranded or double-stranded.

In another embodiment, the present invention provides a method and process of forming fragments which can be used with any shuffling process or combination of shuffling processes. In a further preferred embodiment, a library of mutants from an original gene or family of genes is used as a substrate or substrates for steps comprising denaturing and hybridization. The original gene may be obtained by mutagenic PCR, error-prone PCR, chemical mutagenesis, physical mutagenesis, or a combination thereof. In another preferred embodiment, the step comprising hybridization further comprises creation of heteroduplexes and homoduplexes. The heteroduplexes may then be used after mismatch recognition as substrate or substrates for fragment preparation.

In another embodiment, the present invention provides a method for preparing fragments of DNA for use in polynucleotide shuffling, including exposing at least two homologous heteroduplex polynucleotides to a polynucleotide repair system until the heteroduplexes comprise at least one annealed fragment, and denaturing said heteroduplexes to obtain the fragments. Preferably, this embodiment further comprises, before or after the denaturing or exposing, fragmenting at least one strand of each of said heteroduplexes by further exposing said heteroduplexes to a DNase or restriction enzyme.

In another main embodiment, the invention comprises a template-mediated method of polynucleotide shuffling that includes exposing at least two homologous heteroduplex polynucleotides to a polynucleotide repair system until the heteroduplexes comprise at least one annealed fragment, denaturing the heteroduplexes to obtain the fragments, and hybridizing the fragments to one or more assembly templates to form at least one recombinant polynucleotide. Similarly, this embodiment preferably comprises, before or after the denaturing or exposing, fragmenting at least one strand of each of said heteroduplexes by further exposing said heteroduplexes to a DNase or restriction enzyme.

In a preferred embodiment, the initial library is itself produced by the present invention. In a further preferred embodiment, the initial library may be produced by any shuffling process or combination of shuffling processes. Either in vivo or in vitro screens can be used to form this library for repeating the process of the invention. The recombinant sequences selected after a first running of the process can be optionally mixed with other sequences.

The initial library can also be produced by any method known to one skilled in the art, for example, by starting from a wild-type gene, by successive managed stages of mutagenesis, by error-prone PCR, by random chemical mutagenesis, by random mutagenesis in vivo, or by combining genes of close or relatively distant families within the same or different species. Preferably, the initial library results from chain polymerization reactions under conditions that create random, localized mutations. The invention may also comprise synthetic sequences.

To promote formation of heteroduplexes, embodiments of the invention may include: increasing the number of parent polynucleotides; running the parent polynucleotides through one or more cycles of denaturation and hybridization; using ssDNA sequences to form the heteroduplex parent polynucleotides; or introducing a relative excess of one or more polynucleotides into the initial library to bias heteroduplex formation.

In one embodiment, the parent polynucleotides (which may contain homoduplexes as well as heteroduplexes) are incubated with a mismatch-binding protein such as the mismatch repair complex MutS/MutL/MutH, which recognizes, binds and cuts any mismatch site. This recognition occurs when the opposing template strand (not the assembly template) is methylated. Fragmentation is then amplified with exonucleases. If the cleavage occurs on the 3' side of the mismatch, this step is carried out by exonuclease I, which degrades a single strand only in the 3' to 5' direction. If the cleavage occurs on the 5' side of the mismatch, exonuclease VII or RecJ is used to degrade the single-stranded DNA and produce fragments.

In another embodiment, at least one mismatch is introduced per initial parent polynucleotide. In other embodiments, at least one of the ss or ds initial parent templates (not same as assembly template) is methylated. In other methods, heteroduplexes can be used as substrates for any proteins which can cleave mismatched base pairs in vitro, for example, the complex MutS/MutL/MutH, phage T4 endonuclease VII or phage T7 endonuclease I. In yet another embodiment, artificial mismatches are introduced, for example, by introducing modified nucleotides (dITP or uracil-containing DNA for example) or by creating heteroduplexes between DNA and RNA. In still another embodiment, partial digestion of mismatches is achieved so that all mismatches are not cleaved.

In yet another embodiment, at least one damaged base is introduced per initial parent sequence by all standard known methods, for example mutagenic PCR (e.g., incorporation of base analogs) or by chemical mutagenesis (utilization of: base analogs such as 5-bromouracil or 2-aminopurine; proflavin; alkylation agents like sulfur mustard or nitrogen mustard and ethylmethane sulfonate; deamination agents like nitrous acid; and hydroxylamine or free radicals). After denaturation and hybridization, these molecules can form heteroduplexes with damaged/mismatched bases which can serve as substrates for any proteins of the BER system in vitro. DNA glycosylases can then recognize and excise altered bases by hydrolytic cleavage of the base-sugar bond, generating an AP site. AP endonucleases (for example, human endonucleases such as HAP1, FEN1) then remove AP site and neighboring nucleotides to generate fragments.

In still another embodiment, at least one damaged nucleotide is introduced per initial parent sequence by all standard known methods, for example, by pyrimidine dimer formation induced by UV light. After denaturation and hybridization, these molecules can form heteroduplexes with damaged nucleotides, which can be used as substrates for any proteins of the NER system in vitro. The parent sequences are incubated with a NER system protein such as the Uvr-A/Uvr-B complex, and Uvr-C or RAD, which recognize, bind and cut any resultant damaged nucleotide sites to generate fragments.

EXAMPLES

Example 1

This example depicts the preparation of ss DNA and a parental template.

I. Materials and Methods

A. Oligonucleotides

Figure 4:
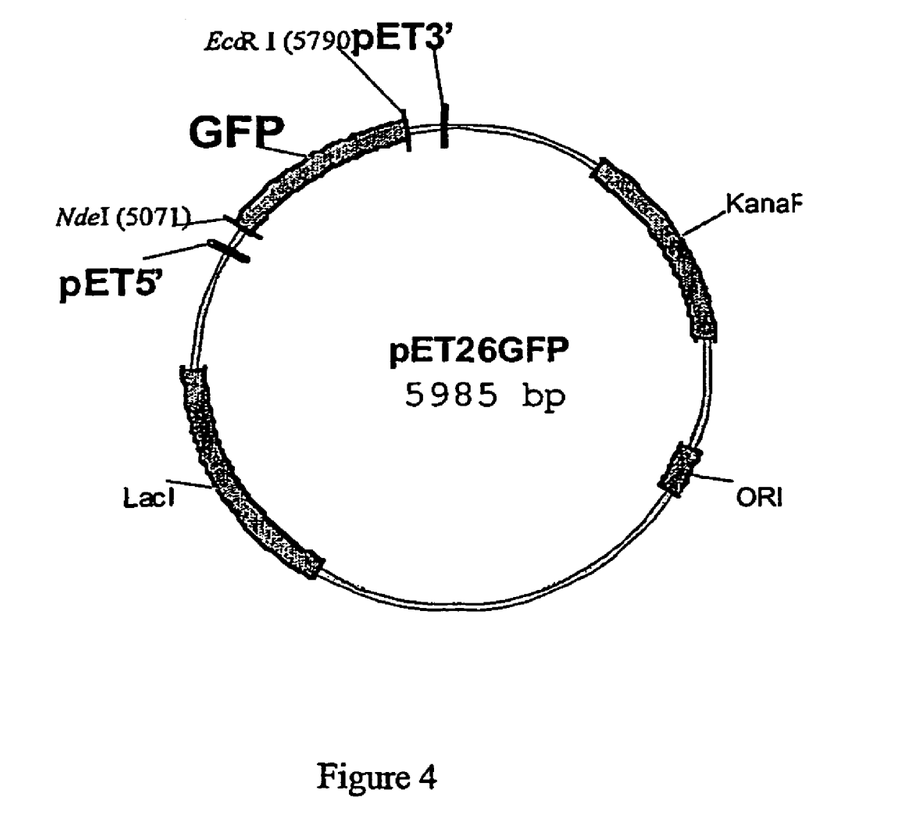
FIG. 4 depicts a plasmid map of PET26GFP.

All synthetic oligonucleotide primers for PCR were by Biotech. The sense primer pET5 5' AGATCTCGATCCCGCGAAATTAATACG3' (SEQ ID NO: 1) and the antisense primer pET3 5' CAAAAAACCCCTCAAGACCCGTTTAG3' (SEQ ID NO: 2) (with or without phosphorothioate (PTO) termination) were used to amplify the GFP gene (GENBANK: AEVGFP) pET26b+cloned (FIG. 4) and make phosphorothioate sense and/or antisense strand.

B. Enzymes

Restriction enzymes, DNA ligase, DNA polymerases, lambda exonuclease were purchased from NEB, and used as recommended by the manufacturers.

II. Results

For the ss DNA template or polynucleotides preparation, several PCR amplifications were done using the following conditions:

(1) two phosphated primers: pET5 P and pET3 P;
(2) two PTO primers: pET5 PTO and pET3 PTO;
(3) a PET5 P primer and a pET3 PTO primer to obtain the ss DNA template after exonuclease treatment; and
(4) a pET3 P primer and a pET5 PTO primer to obtain the ss DNA polynucleotides after exonuclease treatment.

The following PCR program was used:
94° C. 5 min,
(91° C. 30 s, 55° C. 30 s, 72° C. 1.30 min)×30,
72° C. 6 min, 4° C. α.

Figure 5:
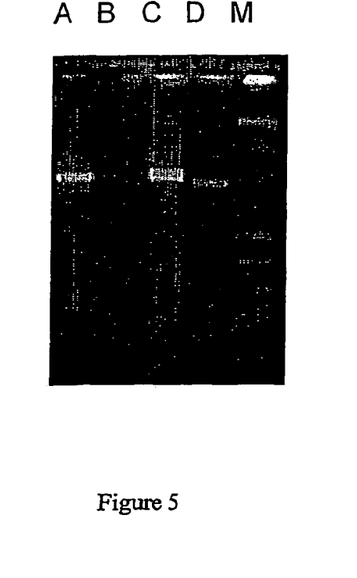
FIG. 5 depicts the results of specific ssDNA preparation using specific lambda exonuclease digestion conditions.
Figure 6:
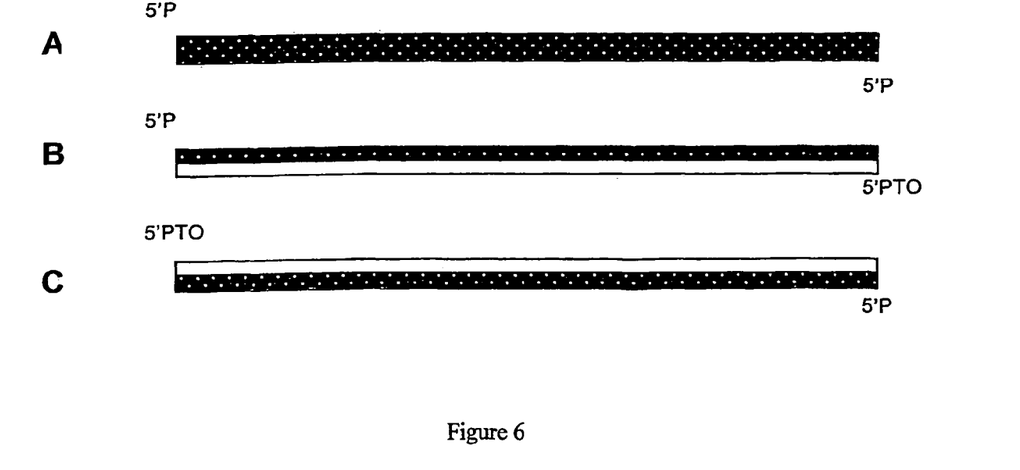
FIG. 6 depicts ssDNA preparation using specific lambda exonuclease the results of specific digestion conditions.

These PCR products were then incubated with or without lambda exonuclease for a selective digestion of 5' P strands, as shown in FIG. 5. Condition (1) resulted in a total lambda exonuclease digestion of pET5 P/pET3 P amplification (see lane B, FIG. 5) compared to the undigested experimental conditions of the same PCR product (see lane A, FIG. 5). Condition (2) resulted in no digestion of PET5 PTO/pET3 PTO amplification (see lane C, Figure 5). Condition (3) resulted in a selective digestion of anti-sense strand resulting in a ss DNA template (see lane D, FIG. 5). Condition (4) resulted in a selective digestion of sense strand resulting in a ss DNA polynucleotides as shown in white (FIG. 6).

Example II

This example depicts fragment preparation using MMR DNA repair.

I. Materials and Methods

MC1061 DE3 cells were used to propagate the expression plasmid pET26b+ (Novagen).

A. Oligonucleotides

All synthetic oligonucleotide primers for PCR were synthetized by MWC Biotech.

B. Enzymes

Restriction enzymes, DNA polymerase, lambda exonuclease, DNA ligase and exonuclease I were purchased from NEB, and used as recommended by the manufacturers.

C. Fragmentation—Assays

Fragmentation assays were carried out in 20 liters containing 0.02 M Tris-HCl (pH 7.6); 5 mM $MgCl_2$; 40 grams bovine serum albumin; 1 mM ATP; an appropriate concentration of each purified MMR proteins and 100 fmol of heteroduplexes. Incubation was achieved at 37° C. for 1 hour and 30 liters of 25 mM EDTA (pH 8.0) was then added. The DNA was purified by phenol extraction and ethanol precipitation. The resuspended DNA was then analyzed on denaturing 1% agarose gel.

II. Results

A. Template preparation, construction of an unactive GFP

Figure 7:
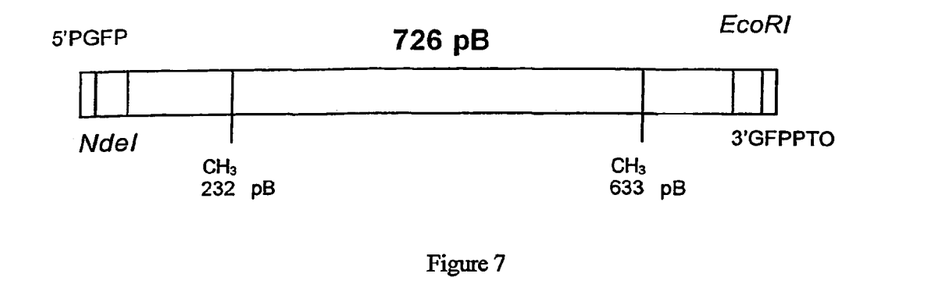
FIG. 7 depicts dam methylase sites.

A PCR amplification of the GFP gene was achieved starting from pET26GFP (compare with FIG. 4) and using 5 PGFP/3 GFPPTO. 1 gram of PCR product resulting from the amplification of GEP gene using pET26GFP as template was then treated with 8 U of dam methylase in order to methylate two specific dam methylase sites GATC as shown in FIG. 7.

Figure 8:
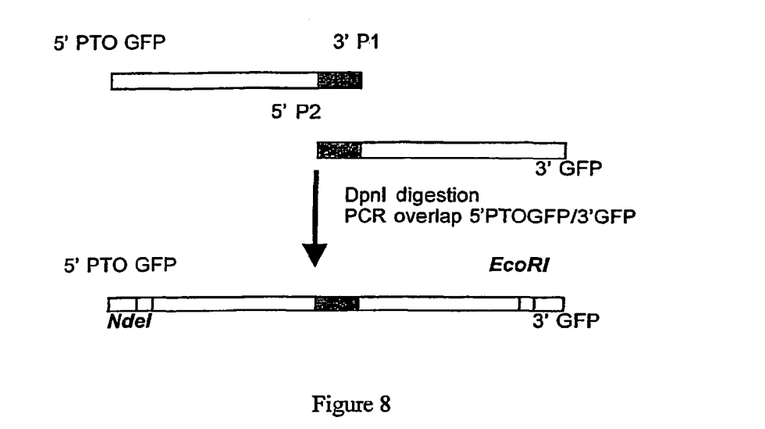
FIG. 8 depicts PCR amplification.

Starting from pET26GFP and using 5 PTOGFP/P1 and P2/3 GFP, we prepared two amplicons in which a small DNA polylinker containing the insertion (FIG. 8, shown in black) was introduced. After DpnI digestion, to remove the plasmid template, a complete GFP gene was amplified using 5 PTOGFP/3 CFP by overlapping PCR using the two previous amplicons as shown FIG. 8.

The PCR product was then digested by Nde/EcoRI and subcloned in pET26b+. The pET26b had been previously linearized by the same restriction enzymes resulting in pETunactGFP which encodes an inactive GFP protein.

B. Heteroduplex Construction

Figure 9:
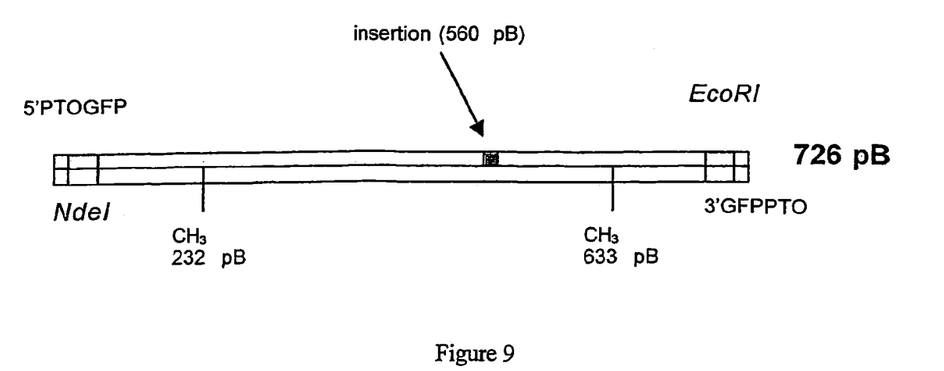
FIG. 9 depicts heteroduplex construction.

The ss DNA were obtained by specific lambda exonuclease digestion (as described in Example I) of the two following amplicons (FIGS. 7 and 8):

(1) amplicon using 5 PGFP/3 GFPPTO specific primers to obtain the anti-sense ss DNA methylated template (as shown in FIG. 9); and (2) amplicon using 5 PTOGFP/3 GFP specific primers to obtain the sense ss DNA with the insertion (as shown in black, FIG. 9).

Heteroduplexes were prepared by annealing an equimolar preparation of ss DNA from the methylated and the unactive GFP gene (with the insertion).

C. Fragmentation Assays Using DNA Repair

Heteroduplexes were then treated with a mixture of purified recombinant MutS, MutL and MutH complex. Fragments of the unmethylated strain were then obtained using uvrD, exonuclease I or VII and SSB activities, as described in materials and methods. After phenol extraction and ethanol precipitation, resuspended DNA was examined on denaturing 1% agarose gel. No fragmentation was detected when no MMR proteins were added. This was in contrast to the two experimental conditions (using (1) exonuclease I, or (2) exonuclease VII) where the following different fragments were observed:

(1) 726,560 and 96 pb (using exonuclease I); and (2) 726,166 and 120 pb (using exonuclease VII).

These results were also reproduced to obtain different fragments for shuffling experiments.

The foregoing presentations are not intended to knit the scope of the invention. Although illustrative embodiments of the present invention have been described in detail and with reference to accompanying drawings, it is obvious to those skilled in the art that modifications to the methods described herein can be implemented. These and other various changes and embodiments may be effected by one skilled in the art without departing from the spirit and scope of the invention, which is intended to be determined by reference to the claims and their equivalents in light of the prior art.

The invention claimed is:

1. A method of obtaining polynucleotide fragments for use in polynucleotide shuffling, comprising:
   (a) obtaining a library of mutant polynucleotides from a parental polynucleotide by mutagenesis;
   (b) denaturing and hybridizing said mutant polynucleotides to form heteroduplex polynucleotides;
   (c) cleaving said heteroduplex polynucleotides by using proteins of a polynucleotide repair system which cleave mismatched base pairs;
   (d) denaturing said cleaved heteroduplex polynucleotides to obtain said polynucleotide fragments; and
   (e) recovering said polynucleotide fragments,
   wherein before exposing said heteroduplex polynucleotide to said polynucleotide repair system, formation of said heteroduplex polynucleotide is promoted by increasing the number of the parent polynucleotides in said library relative to other polynucleotides in said library.

2. The method of claim 1, wherein said method occurs in vitro.

3. The method of claim 1, wherein said heteroduplex polynucleotides are generated from a native gene by successive directed mutagenesis, by error-prone PCR, by random chemical mutagenesis, or by in vivo random mutagenesis.

4. The method of claim 1, wherein said fragments are non-identical.

5. The method of claim 1, wherein said polynucleotide repair system comprises mismatch repair enzyme, base excision repair enzyme, nucleotide excision repair enzyme, phage T4 endonuclease VII, phage T7 endonuclease I, or a combination of enzymes thereof.

6. The method of claim 5, wherein said mismatch repair enzyme is DAM methylase, MutS, MutL, MutH, exonuclease, DNA helicase II, SSB protein, or a combination of enzymes thereof.

7. The method of claim 5, wherein said base excision repair enzyme is DNA glycosylase, AP endonuclease, or a combination of enzymes thereof.

8. The method of claim 5, wherein said nucleotide excision repair enzyme is Uvr-A, Uvr-B, Uvr-C, or a combination of enzymes thereof.

9. The method of claim 1, wherein said using proteins of a polynucleotide repair system comprises incubating said heteroduplex polynucleotide with phage T4 endonuclease VII, or a combination of enzymes thereof.

10. The method of claim 1, wherein said heteroduplex polynucleotides comprise dITP or uracil-containing DNA.

11. The method of claim 1, wherein said heteroduplex polynucleotides comprise a heteroduplex between DNA and RNA.

12. The method of claim 1, wherein said polynucleotide repair system partially digests and partially cleaves mismatches.

* * * * *

SEQUENCE LISTING

<160> NUMBER OF SEQ ID NOS: 2

<210> SEQ ID NO 1
<211> LENGTH: 27
<212> TYPE: DNA
<213> ORGANISM: Artificial
<220> FEATURE:
<223> OTHER INFORMATION: Primer
<220> FEATURE:
<221> NAME/KEY: Primer
<222> LOCATION: (1)..(27)
<223> OTHER INFORMATION: Sense primer pET5'

-continued

```
<400> SEQUENCE: 1
agatctcgat cccgcgaaat taatacg                                         27

<210> SEQ ID NO 2
<211> LENGTH: 26
<212> TYPE: DNA
<213> ORGANISM: Artificial
<220> FEATURE:
<223> OTHER INFORMATION: Primer
<220> FEATURE:
<221> NAME/KEY: Primer
<222> LOCATION: (1)..(26)
<223> OTHER INFORMATION: Antisense primer pET3'

<400> SEQUENCE: 2
caaaaaaccc ctcaagaccc gtttag                                          26
```